(12) United States Patent
Wang

(10) Patent No.: US 10,542,881 B2
(45) Date of Patent: Jan. 28, 2020

(54) ELECTRIC SLIT WIDTH ADJUSTING SYSTEM OF SLIT-LAMP MICROSCOPE

(71) Applicant: Kang Hua Rui Ming Science and Technology CO., LTD., Chongqing (CN)

(72) Inventor: Yi Wang, Chongqing (CN)

(73) Assignee: KANG HUA RUI MING SCIENCE AND TECHNOLOGY CO., LTD., Chongqing (CN)

( * ) Notice: Subject to any disclaimer, the term of this patent is extended or adjusted under 35 U.S.C. 154(b) by 98 days.

(21) Appl. No.: 15/944,810

(22) Filed: Apr. 4, 2018

(65) Prior Publication Data
US 2018/0289255 A1  Oct. 11, 2018

(30) Foreign Application Priority Data

Apr. 11, 2017 (CN) .......................... 2017 1 0231740

(51) Int. Cl.
*A61B 3/00* (2006.01)
*A61B 3/135* (2006.01)

(52) U.S. Cl.
CPC ............ *A61B 3/0075* (2013.01); *A61B 3/135* (2013.01)

(58) Field of Classification Search
CPC .............................. A61B 3/0075; A61B 3/135
See application file for complete search history.

*Primary Examiner* — Jack Dinh
(74) *Attorney, Agent, or Firm* — Gokalp Bayramoglu

(57) ABSTRACT

The present invention is an electric slit width adjusting system of a slit-lamp microscope consisting of a light slit width adjusting mechanism of the slit lamp, an adjustment motor and a teletype operating mechanism. The light slit width adjusting mechanism of the slit lamp includes a mechanical drive controlling the slit width. The adjustment motor is arranged on the light slit width adjusting mechanism and controlled by the teletype operating mechanism through electrical signals. The teletype operating mechanism with a function of precisely controlling the rotation angle of the adjustment motor is arranged above the operating handle of slit lamp mobile platform (or the base of slit lamp mobile platform).

3 Claims, 2 Drawing Sheets

ELECTRIC SLIT WIDTH ADJUSTING SYSTEM OF SLIT-LAMP MICROSCOPE

CROSS REFERENCE TO RELATED APPLICATIONS

This application is based upon and claims priority to Chinese Patent Application No. 201710231740.X, filed on Apr. 11, 2017, the entire contents of which are incorporated herein by reference.

TECHNICAL FIELD

The present invention relates to an adjusting system, in particular to an electric slit width adjusting system of a slit-lamp microscope.

BACKGROUND OF THE INVENTION

A slit-lamp microscope is an essential pathological diagnosis instrument for ophthalmologic examination. A slit-lamp microscope system used for the discipline normally comprises a slit light generation device and an optical microscope. An operator, when using the slit lamp of prior art, should hold the operating handle of slit lamp mobile platform with one hand and rotate the rotary knob to adjust the slit width with the other hand. As a result, the inconvenience caused by interruption of operation is inevitable if something else needs to be done by hand (for example keeping the eyes of a patient open and adjusting optical magnification). Meanwhile, the slit width adjusting mechanism of the slit light generation device comprises a set of stepped mechanical drive structure, which rotates the eccentric cam through the hand-wheel rotating mechanism to push a long push rod. The long push rod drives the top block to push the short push rod. The short push rod drives the slit cam to push against the cylinder with slit and move the slit blocks connected with the cylinder with slit to adjust the slit width. The adjustment method has low accuracy and poor reliability due to complicated steps and structures.

In order to solve the problems above, it is necessary to reduce the intermediate links of transmission, replace the complicated hand wheel-controlled mechanical transmission with the teletype control, control the newly designed slit width adjusting mechanism using adjustment motor and move the slit blocks connected with the cylinder with slit to adjust the slit width. Further, the mechanical rotation by the hand wheel is replaced with the precise rotation by the adjustment motor so as to improve the accuracy and comfort of the slit light control and cut down the expenditures of machining. Meanwhile, the operating component controlling the rotation of the adjustment motor may also be arranged on the parts other than slit light generation device, such as operating handle of slit lamp mobile platform and slit lamp mobile platform base. Therefore, the structural function improvement is implemented thereof.

SUMMARY OF THE INVENTION

The purpose of the present invention is to provide an electric slit width adjusting system of a slit-lamp microscope to solve the problems raised from the background.

In order to achieve the purpose, the present invention provides the following solutions.

An electric slit width adjusting system of a slit-lamp microscope includes a light slit width adjusting mechanism of a slit lamp, an adjustment motor and a teletype operating mechanism. The electric slit width adjusting system includes an adjustment motor 1, a cam 2, a rotation shaft 3, an adapter sleeve 4, a hand-wheel cap 5, two fixed shafts 6, two springs 7, a cylinder with slit 8, two fixed shaft sleeves 9, two small bearings 10, two slit blocks 11, a slit shell 12, four washers 13 and two back shafts 14; the cam 2 and the hand-wheel cap 5 are connected with the rotation shaft, the rotation shaft 3 rotates to drive the rotation of the cam 2, and the cam 2 makes the assemblies on both sides of the cylinder with slit 8 spin around the fixed small shafts 6 in the opposite directions to change the distance between two slit blocks 11. The contours of the cam 2 are two cam curves with symmetrically changed width; the cam 2 may be driven by the adjustment motor 1 or by rotating the hand-wheel cap 5 manually; the adjustment motor 1 driving the cam 2 is controlled by the teletype operating mechanism arranged above the operating handle of slit lamp mobile platform (or slit lamp mobile platform base) through the electrical signals. The light slit width adjusting mechanism of slit-lamp microscope for medical ophthalmology is rearranged from the slit lighting assembly to the operating handle of slit lamp mobile platform (or slit lamp mobile platform base) in the present invention to simplify the complex mechanical transmission with the electronic control, further improve the convenience, comfort and accuracy of the slit width adjusting operation, and assist the operator in operation. The light slit width adjusting mechanism of slit lamp comprises a mechanical drive controlling the slit width; the adjustment motor is arranged on the light slit width adjusting mechanism and controlled by the teletype operating mechanism through electrical signals.

Further, the teletype operating mechanism is arranged above the operating handle of slit lamp mobile platform (or slit lamp mobile platform base).

Further, the teletype operating mechanism has a function of precisely controlling the rotation angle of the adjustment motor.

Compared with the prior art, the advantages of present invention are as follows.

The slit width adjusting system of a slit-lamp microscope for medical ophthalmology is simplified in the present invention by rearranging the operation of slit width to the operating handle of slit lamp mobile platform (or slit lamp mobile platform base) to reduce the complicated intermediate transmission, further improve the convenience, comfort and accuracy of the light slit width adjusting operation, and make it possible to make up a conventional mechanism using the simplified ophthalmic slit-lamp microscope.

DETAILED DESCRIPTION OF THE INVENTION

The technical solution according to the embodiments of the present invention will be described clearly and completely as follows in combination with the drawings of these embodiments. Apparently, the embodiments described are only some embodiments of the invention, but not all embodiments. Based on the embodiments of the invention, all other embodiments obtained by those of ordinary skill in the art without making creative work are within the protection scope of the invention.

Figure 1:
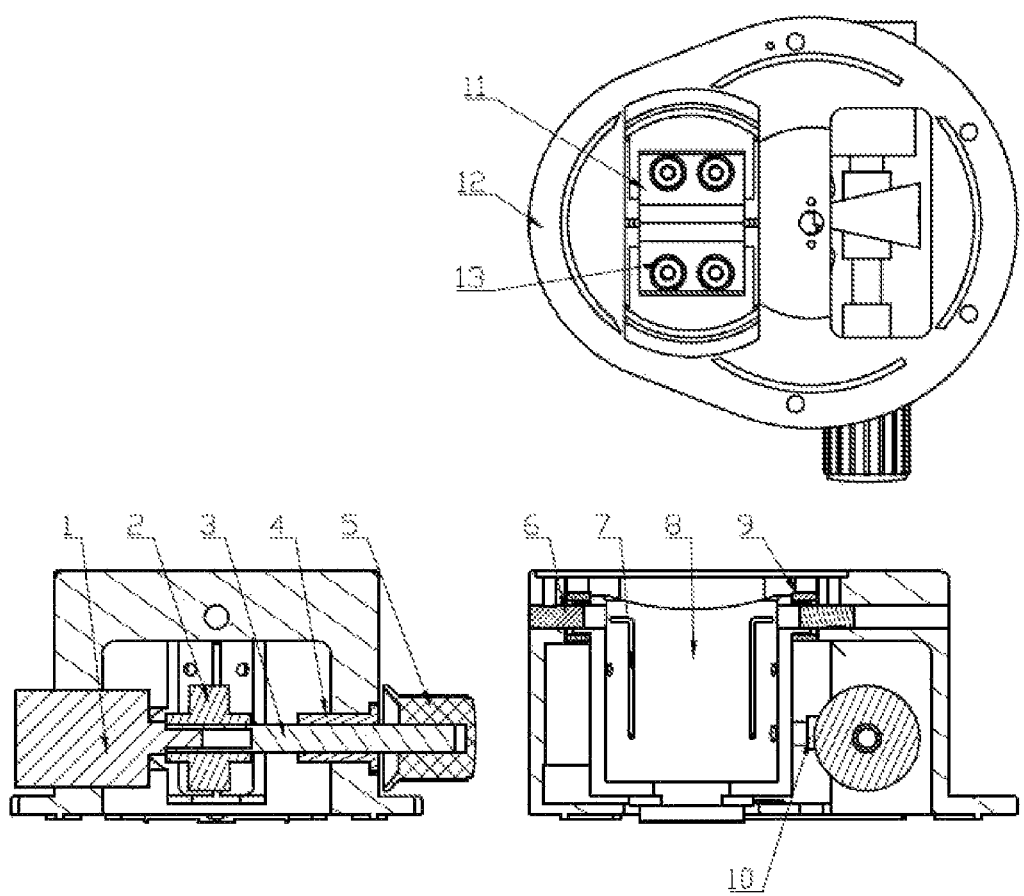
FIG. 1 is a section view of the invention.
Figure 2:
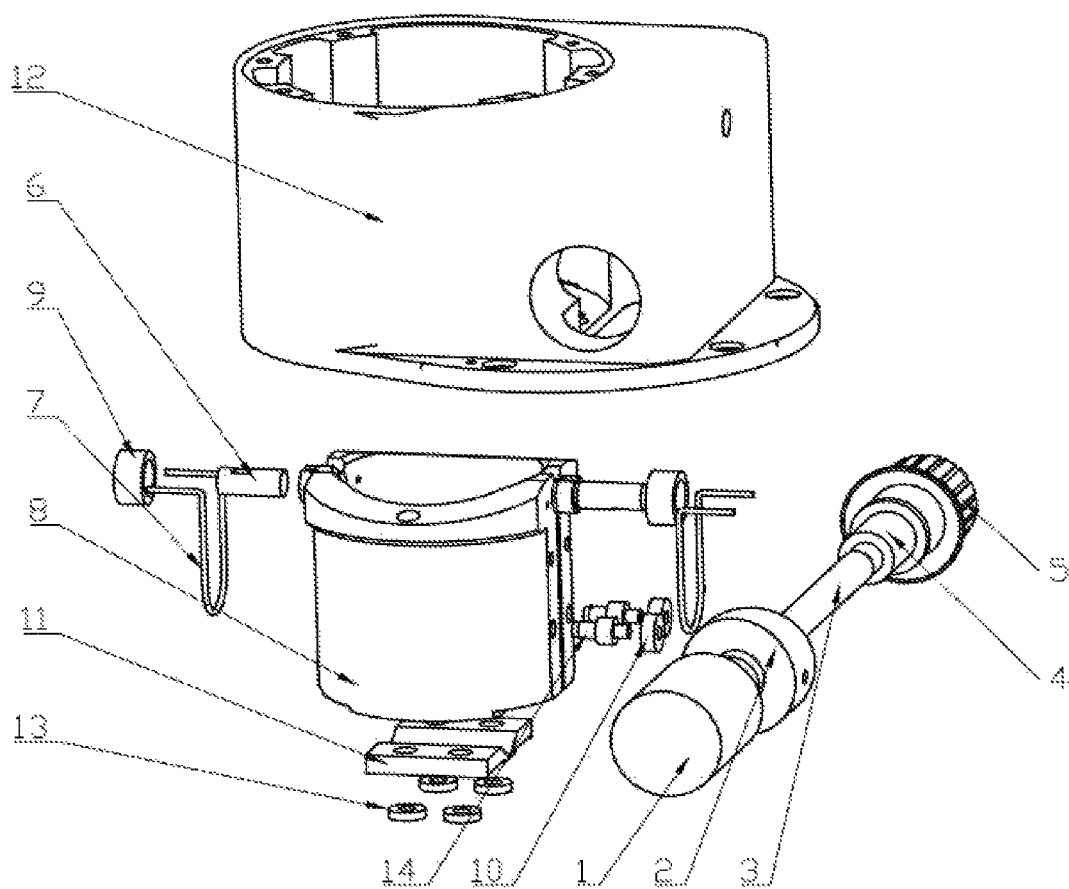
FIG. 2 is an exploded view of the invention.
Figure 3:
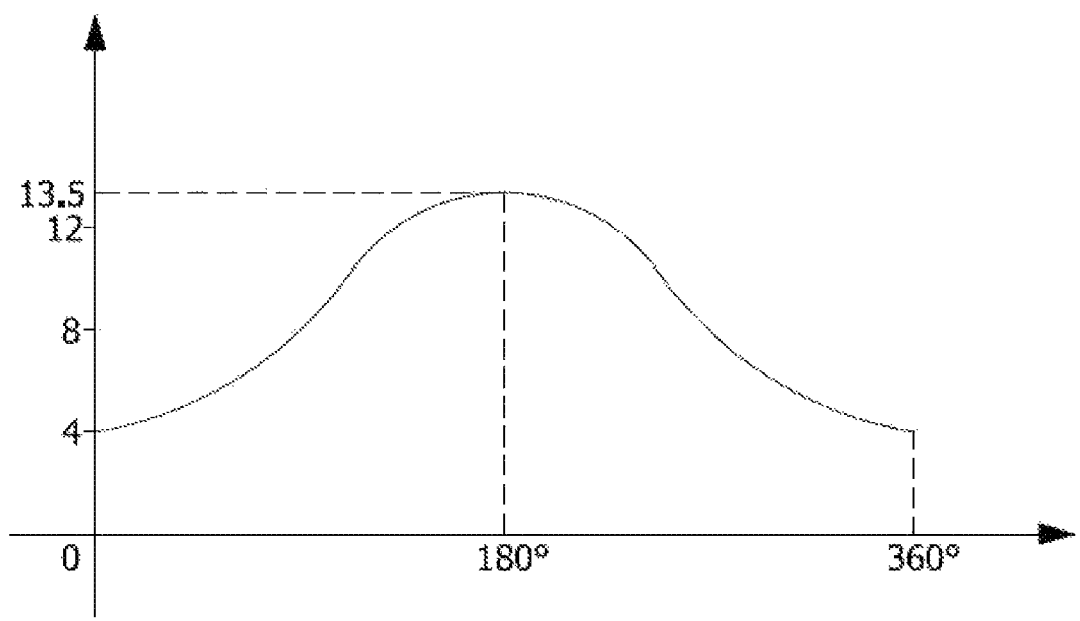
FIG. 3 is a slit width curve diagram of the invention.

Referring to FIG. 1 to FIG. 3, an electric slit width adjusting system of a slit-lamp microscope according to the embodiments of the present invention includes a light slit width adjusting mechanism of a slit lamp, an adjustment motor and a teletype operating mechanism. The electric slit width adjusting system comprises an adjustment motor 1, a cam 2, a rotation shaft 3, an adapter sleeve 4, a hand-wheel cap 5, two fixed shafts 6, two springs 7, a cylinder with slit 8, two fixed shaft sleeves 9, two small bearings 10, two slit blocks 11, a slit shell 12, four washers 13 and two back shafts 14; the cam 2 and the hand-wheel cap 5 are connected with the rotation shaft, the rotation shaft 3 rotates to drive the rotation of the cam 2, and the cam 2 makes the assemblies on both sides of the cylinder with slit 8 spin around the fixed small shafts 6 in the opposite directions to change the distance between two slit blocks 11. The contours of the cam 2 are two cam curves with symmetrically changed width; the cam 2 may be driven by the adjustment motor 1 or by rotating the hand-wheel cap 5 manually; the adjustment motor 1 driving the cam 2 is controlled by the teletype operating mechanism arranged above the operating handle of slit lamp mobile platform (or slit lamp mobile platform base) through the electrical signals. The light slit width adjusting mechanism of slit-lamp microscope for medical ophthalmology is rearranged from the slit lighting assembly to the operating handle of slit lamp mobile platform (or slit lamp mobile platform base) in the present invention to simplify the complex mechanical transmission with the electronic control, further improve the convenience, comfort and accuracy of the slit width adjusting operation, and assist the operator in operation.

Specifically, after receiving a data signal from the computer, the adjustment motor 1 starts rotating to drive the cam 2 to rotate together. The cam has a non-unique curve (as shown in FIG. 3). To adjust the slit width, different parts of the cam 2 contact with the small bearings 10 by selecting corresponding angles to determine the distance between two slit blocks. The slit widths vary with the rotation angles set according to data signals received by the adjustment motor 1. The slit width may be controlled precisely by setting a precise rotation angle of the adjustment motor. The operating component controlling the rotation of the adjustment motor may also be arranged on the parts other than the slit light generation device, such as operating handle of slit lamp mobile platform and slit lamp mobile platform base.

It will be apparent to a person skilled in the art that the present invention should not be restricted to the above detailed embodiments and may be realized by other embodiments without departing from the spirit or basic features of the invention. As a result, for all intents and purposes, these embodiments should be considered as being illustrative rather than restrictive. The scope of the invention is defined by the appended claims rather than description above, so as to include all changes fallen into the contents and scope of the equivalent essential elements of claims into the invention. The reference numbers in appended drawings shall not be construed as limiting related claims.

In addition, it should be understood that every embodiment may include more than one independent technical solution whereas the embodiment described in the specification. The description of the specification is for clarity only. A person skilled in the art should treat the specification as a whole, and the technical solutions of all embodiments may be properly combined to form other embodiments that may be understood by a person skilled in the art.

I claim:

1. An electric slit width adjusting system of a slit-lamp microscope, comprising
 a light slit width adjusting mechanism of a slit lamp, an adjustment motor and a teletype operating mechanism, a cam, a rotation shaft, an adapter sleeve, a hand-wheel cap, two fixed shafts, two springs, a cylinder with slit, two fixed shaft sleeves, two small bearings, two slit blocks, a slit shell, four washers and two back shafts; wherein
 the cam and the hand-wheel cap are connected with the rotation shaft, the rotation shaft rotates to drive a rotation of the cam, and the cam makes a plurality of assemblies on both sides of the cylinder with slit spin around the fixed shafts in an opposite direction to change a distance between the two slit blocks;
 a contour of the cam are two cam curves with symmetrically changed width; the cam may be driven by the adjustment motor or by rotating the hand-wheel cap manually; the adjustment motor driving the cam is controlled by the teletype operating mechanism through a plurality of electrical signals;
 the light slit width adjusting mechanism of the slit lamp comprises a mechanical drive controlling a slit width; the adjustment motor is arranged on the light slit width adjusting mechanism and controlled by the teletype operating mechanism through the plurality of electrical signals.

2. The electric slit width adjusting system of the slit-lamp microscope of claim 1, wherein the teletype operating mechanism is arranged above an operating handle of a slit lamp mobile platform or a base of a slit lamp mobile platform.

3. The electric slit width adjusting system of the slit-lamp microscope of claim 1, wherein the teletype operating mechanism has a function of precisely controlling a rotation angle of the adjustment motor.

* * * * *